United States Patent
Khir (10) Patent No.: US 10,441,694 B2
(45) Date of Patent: Oct. 15, 2019

(54) MEDICAL BALLOON

(71) Applicant: Brunel University London, Uxbridge (GB)

(72) Inventor: Ashraf Khir, Uxbridge (GB)

(73) Assignee: Brunel University London (GB)

( * ) Notice: Subject to any disclaimer, the term of this patent is extended or adjusted under 35 U.S.C. 154(b) by 0 days.

(21) Appl. No.: 15/210,551

(22) Filed: Jul. 14, 2016

(65) Prior Publication Data
US 2017/0014563 A1    Jan. 19, 2017

(30) Foreign Application Priority Data

Jul. 15, 2015 (GB) .................................. 1512389.6

(51) Int. Cl.
*A61M 1/10* (2006.01)
*A61M 25/10* (2013.01)
*A61M 1/12* (2006.01)

(52) U.S. Cl.
CPC .......... *A61M 1/1037* (2013.01); *A61M 1/106* (2013.01); *A61M 1/1072* (2013.01); *A61M 1/1096* (2014.02); *A61M 1/125* (2014.02); *A61M 25/1002* (2013.01); *A61M 25/1018* (2013.01); *A61M 1/122* (2014.02); *A61M 2025/102* (2013.01)

(58) Field of Classification Search
CPC .......................... A61M 25/10; A61M 25/1011
See application file for complete search history.

(56) References Cited

U.S. PATENT DOCUMENTS

| | | | | |
|---|---|---|---|---|
| 2004/0267197 A1* | 12/2004 | Blankenship | ........... | A61F 2/958 604/103.06 |
| 2009/0254064 A1* | 10/2009 | Boatman | ............ | A61M 25/1011 604/509 |
| 2015/0224290 A1* | 8/2015 | Chanduszko | ........... | A61F 2/958 600/585 |

* cited by examiner

*Primary Examiner* — Jon Eric C Morales
(74) *Attorney, Agent, or Firm* — Richard Blakely Glasgow (57) ABSTRACT

A medical balloon for a balloon pump is disclosed. The medical balloon has a first end and a second end and a port at one of the ends for engaging a catheter for receiving an inflation fluid into the balloon. The balloon has one or more exterior walls defining, when the balloon is inflated at substantially a standard operating pressure, a taper along at least a part of the length of the balloon. The taper has two or more consecutive tapering sections, each tapering section having a different, substantially constant, angle of tapering. The balloon is substantially asymmetrical about a mid-point between the first and second ends when inflated.

18 Claims, 9 Drawing Sheets

MEDICAL BALLOON

CROSS-REFERENCE TO RELATED APPLICATIONS

This application claims priority to GB Patent Application No. 1512389.6 filed on Jul. 15, 2015, the complete disclosure of said application is hereby incorporated by reference.

FIELD OF THE INVENTION

The present invention relates to medical balloons and in particular (but not exclusively) to Intra-Aortic Balloons (IABs) for use in intra-aortic balloon pumping with humans or animals.

BACKGROUND TO THE INVENTION

Medical balloons are used in a number of areas in treatment of humans and animals. For example, balloons are used during delivery of medical devices such as stents. A deflated balloon is positioned inside a stent and the package is positioned in a lumen that the stent is to support. The balloon is inflated which causes the stent to expand into a deployed state. The balloon can then be deflated and removed, leaving the deployed stent in place.

Embodiments of the present invention concern medical balloons that are designed for use in pumping. Preferred embodiments concern intra-aortic balloons for use in intra-aortic balloon pumps. IABs are well known for use in treating patients with heart failure and other cardiac pathologies, in order to increase blood flow to coronary arteries and decrease ventricular load.

The two main benefits of the IAB therapy are achieved as follows:

1) To increase flow to the coronary artery. This benefit is achieved through balloon inflation, which results in displacing an amount of blood towards the ascending aorta, increasing the pressure at the coronary sinus, and hence enhancing the flow to the coronary arteries.
2) To decrease the load against which the heart pumps. This benefit is achieved through balloon deflation, which reduces the pressure at the root of the aorta. Consequently, when the aortic valve opens, the heart experiences less pressure which reduces the mechanical work required by the heart to eject its blood output into the aorta. This also reduces the amount of oxygen required by the heart muscle and may allow it to rest.

An IAB is used to operate as a pump; inflation and deflation causes blood to flow predominantly towards and away from the left ventricle respectively. This pump acts as a mechanical device that is operated to increase coronary flow and therefore improve myocardial oxygen delivery. The IAB is typically connected via a catheter to an external pump. The IAB is inflated and deflated in synchronisation with heartbeats, in a manner known as counter-pulsation. Typically, the IAB is inflated in early diastole (i.e. immediately following closure of the aortic valve) in order to displace blood towards the coronary arteries. It is considered that a balloon is more efficient if it can maximise this fluid towards the ascending aorta.

The IAB is typically then deflated in late diastole (i.e. immediately prior to the left ventricle's contraction) to reduce the load (afterload) and hence reduces ventricular oxygen.

The IAB is normally introduced into the body at a site remote of the heart such as the groin and then guided up the aorta towards the heart. The IAB is packaged in such a way as to minimise its profile to allow for insertion from the femoral artery. The catheter that is attached to the IAB is used to provide fluid (typically helium which is selected due to its low viscosity and inert nature) for inflation and deflation.

The hydrostatic pressure experienced along the length of conventional, nominally cylindrical IABs, inserted into the aorta of an inclined patient, causes them to inflate from top to bottom (proximal from and distal to the heart respectively). The inventor of the present application has also observed that this combination of pressure gradient and shape will displace less blood towards the heart than is desirable. As such, it is common for conventional prior art IABs to provide reduced efficacy in the inclined patient. These observations were first noted by the inventor in the publication Khir A W, Price S, Hale C, Young D A, Parker K H, Pepper J R. Intra-Aortic Balloon Pumping: Does Posture Matter? Artif Organs, 29: 36-40, 2005.

One particular issue with IAB treatment is the possibility of mechanical damage to blood cells. As the IAB is inflated or deflated, displacement pressures and/or pumping/suction forces are applied to blood cells. If these or their rates are too extreme, it may result in damage to the blood cells. There is also a risk that blood cells may be trapped between the IAB and a vessel wall if the IAB is operated to occlude the passage or vessel. A blood cell may burst if subjected to pressures of above or lower than 200 Pa.

In the present application, certain terms are used and should be understood as follows:

intra-aortic balloon (IAB), the device inserted into a patient's aorta first end of an IAB, the lower end, bottom or base, distal from the heart (the end at which the catheter connects)

second end of an IAB, the upper end, top or tip, proximal to the heart (the opposite end from the catheter connection)

length of an IAB, the longitudinal length of an IAB length of a tapered section; the length, from the start of the taper to the point where the taper ends (for example, where it makes a point at an end of the balloon or where the balloon walls become non-tapering), along the longitudinal axis of an IAB intra-aortic balloon pump (IABP); the instrument external to the patient that pumps gas (usually helium) to an IAB via a catheter. It will be appreciated that there are effectively two "pumps" in an IABP: the external pump that supplies the gas via the catheter to the IAB, and, the IAB itself which when inflated and deflated in the aorta causes pumping of blood.

inflation; the expansion of the cross-sectional area of an IAB when pressurised gas is pumped into its internal chamber(s)

fully inflated; the state of the balloon when its walls are completely inflated to reach their sectional nominal dimensions in response to the standard manufacturer inflation pressure or higher.

pump/pumping; the pumping effect exerted by an IAB on blood in the aorta.

STATEMENT OF THE INVENTION

According to the present invention, there is provided a medical balloon for a balloon pump, the medical balloon having a first end and a second end and a port at one of the ends for engaging a catheter for receiving an inflation fluid into the balloon, the balloon having one or more exterior walls defining, when the balloon is inflated at substantially a standard operating pressure, a taper along at least a part of the length of the balloon, the taper having two or more consecutive tapering sections, each tapering section having a different, substantially constant, angle of tapering, the balloon being substantially asymmetrical about a mid-point between the first and second ends when inflated.

Preferably, the balloon is fully inflated at the standard operating pressure.

The taper may be a first taper that tapers along the length of the balloon towards one of the first or second ends, the balloon further comprising a second taper having one or more tapering sections that taper along the length of the balloon towards the other of the first or second ends.

The first taper may expand towards its respective end and the second taper contracts towards its respective end.

The first taper may contract towards its respective end and the second taper expands towards its respective end.

The first and second tapers may contract towards their respective ends.

The first and second tapers may expand towards their respective ends.

The exterior walls may further define, when the balloon is inflated at substantially a standard operating pressure, a substantially non-tapering section, the substantially non-tapering section being at least ⅓ the longitudinal length of the balloon.

The exterior wall thickness may increase along at least a part of the length of the balloon.

The exterior wall thickness may increase towards the second end.

The balloon may be adapted for preferential inflation from the first end to the second end.

The balloon may comprise an elastic polymer.

The balloon may comprise two or more portions, and wherein the two or more portions are formed from elastic polymers having different mechanical properties.

The balloon may comprise a single chamber.

The balloon may comprise two or more chambers separated by one or more septa.

The one or more septa may include one or more orifices.

The one or more septa may include one or more one-way valves.

The balloon may comprise two or more chambers.

The medical balloon may further comprise a port associated with each chamber, each port engaging a respective catheter for separately supplying an inflation fluid to the port's respective chamber.

The balloon may include a port at each of the first and second ends and being arranged to engage the catheter at either of the first and second ends, the balloon further including a plug to plug the port of the first or second end not engaging the catheter.

Preferably, the balloon is an intra-aortic balloon, IAB

The present invention seeks to address one or more problems associated with medical balloons for balloon pumping and in particular to problems with known IABs.

An advantage of embodiments of the present invention is that, during inflation, the medical balloon preferentially pumps more blood in a direction extending from the first end of the medical balloon towards the second end of the medical balloon.

Embodiments of the present invention preferably include a tapered section at the second end proximal to the heart in order to improve the pumping efficiency of the medical balloon. Despite the fact that such embodiments may still inflate from top to bottom, it has been found that there is an improved pumping action due to the presence of the tapered section at the top of the balloon. This is because of the progressive decrease of the balloon's cross-sectional area along its length towards the second end, which presents the fluid outside the balloon with less resistance towards the second end than the first end, compared to a standard cylindrical balloon.

In alternate embodiments, there may be a taper instead at the first end distal to the heart or there may be tapers at both ends.

In a preferred embodiment, the balloon includes a substantially cylindrical section of at least ⅓ the overall longitudinal length of the balloon.

In optional embodiments, the IAB is adapted for preferential inflation (either progressively or sequentially) from the first end of the IAB towards the second end. Such preferential inflation from the first end to the second end results in further improvements in pumping efficiency and is also generally unaffected by the orientation of the patient when in use.

In some embodiments the balloon may be anisotropic, i.e. the balloon may have a characteristic (e.g. diameter, wall thickness or wall material) that varies from the first end to the second end, longitudinally along the balloon. In other embodiments the IAB may have two or more balloons or a single balloon divided into two or more chambers.

Inflation Effects

As discussed above, the inventor observed that when a conventional IAB is operated at an angle, such as when a patient is inclined to the preferred semi-recumbent position, the resulting hydrostatic pressure difference between the ends of the balloon will cause such a conventional IAB to inflate progressively from the second end towards the first end (i.e. from top to bottom). This difference in hydrostatic pressure, Δp, is given by:

$$\Delta p = \rho * g * h$$

where: ρ=density of blood
  g=gravitational acceleration
  h=vertical difference in height between the two ends of the IAB Deflation Effects The preferred direction of IAB deflation is from tip to base; and similarly, the preferred direction of the decompression action is also from the tip to the base of the balloon. The mechanical effect of balloon deflation is understood as follows: as the balloon begins to deflate, it generates an expansion (decompression) wave that runs towards the ascending aorta. By its nature, this wave pulls an amount of blood away from the heart (similar to drawing fluid through a straw).

The inventor observed that when the balloon is operated at an angle to the horizontal, the balloon begins to deflate from the base to the tip. This is due to the hydrostatic pressure difference between the two ends of the balloon; with the higher pressure acting at the base pushing the helium out of the balloon. At the onset of deflation blood is being drawn away from the ascending aorta, it faces a hydraulic resistance because, at that moment, the upper portion of the IAB is still in its inflated condition. This resistance is a function of the cross-sectional area of the balloon at the tip region and this is particularly acute for conventional balloons.

However, the cross-sectional area of the region approaching the top of the balloon in embodiments of the present invention is much smaller than that of the conventional balloon. As such, it presents less resistance and hence allows for enhanced reduction of the afterload.

Preferably, embodiments of the present invention are operated and sized so as to be non-occluding.

While embodiments of the present invention have been presented for use in intra-aortic balloon pumping, it will be appreciated that they could also be used for balloon pumping elsewhere.

BRIEF DESCRIPTION OF THE DRAWINGS

Embodiments of the present invention will now be described in detail, by way of example only, with reference to the accompanying drawings in which balloons are illustrated in their fully inflated state and in which.

DETAILED DESCRIPTION

Figure 1:
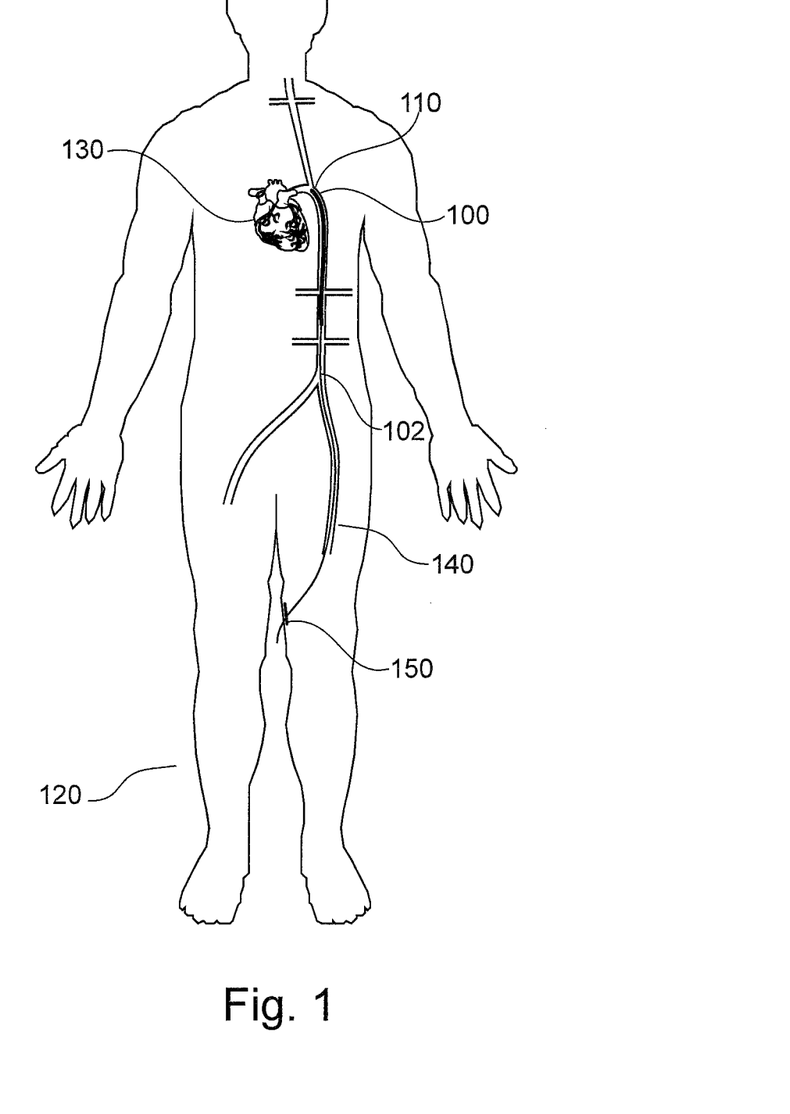
FIG. 1 is a schematic diagram showing a medical balloon in the form of an IAB according to a first embodiment inserted into the aorta of a human patient.

FIG. 1 shows a medical balloon in the form of an IAB 100 according to a first embodiment. The IAB 100 is shown within the aorta 110 of a human patient 120. The IAB 100 is connected to a catheter in the form of a flexible pipe 102.

In this embodiment, the balloon is made of a polymeric material and the flexible catheter 102 is typically made from a grade of polyurethane or other polymer of similar properties.

The aorta 110 extends from the heart 130 of the patient 120 toward a groin region 140 of the patient 120 (the aorta 110 also supplies other portions of the patient 120 with oxygenated blood but, for clarity, FIG. 1 only shows the aorta 110 descending down to the groin area 140 of the patient 120).

To position the IAB 100 inside the aorta 110 close to the heart 130, a clinician (not shown) typically makes an incision 150 in the groin area 140 and uses the catheter 102 to guide the IAB 100 until the top end (see FIGS. 2a and 2b, which show the top end of the balloon 101 as a second end 202; and FIG. 4) of the balloon 101 is near the heart 130. In some embodiments, the IAB 100 may comprise a radiopaque X-ray contrast medium to assist in the positioning of the IAB 100. Thus the IAB 100 is moved from a downstream (distal the heart 130) region of the aorta 110 to an upstream region (proximal the heart 130) of the aorta 110.

Once in position, the IAB 100 is inflated by pumping helium via the catheter 102 into the balloon 101. Deflation is achieved by evacuating helium from the balloon via the catheter 102.

Although the IAB is illustrated in connection with at least selected embodiments as being connected to an external pump via a catheter, it will be appreciated that the IABs may be produced and sold separately to external pumps.

Figure 2A:
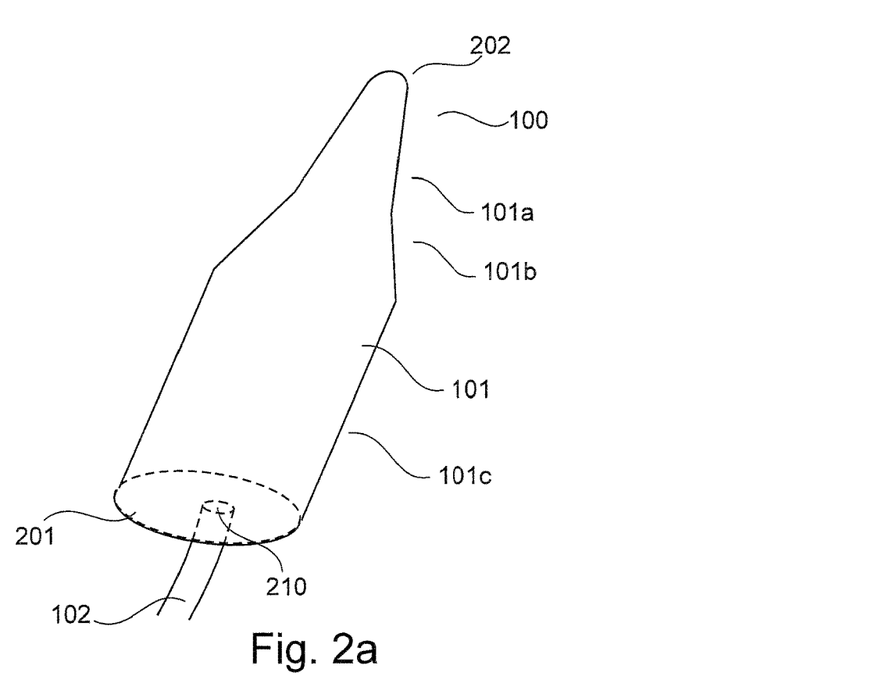
FIG. 2a is a sectional view of the IAB of the first embodiment in more detail.

FIG. 2a shows the IAB 100 of the first embodiment in more detail, and shows that the balloon 101 has a first end and a second end and a port at one of the ends for engaging a catheter 102 for receiving an inflation fluid into the balloon, the balloon having one or more exterior walls defining, when the balloon is fully inflated at substantially a standard operating pressure, a taper along the length of the balloon, the taper having two tapering sections 101a, 101b, each tapering section 101a, 101b having a different, substantially constant, angle of tapering with respect to a longitudinal axis (X, shown in FIG. 2b) of the balloon 101.

In the illustrated embodiment, the tapered sections 101a, 101b reduce in diameter from a first end 201 to a second end 202. In this embodiment the balloon has, when fully inflated, a length of approximately 27 cm and a diameter of approximately 1.5 cm at the first end 201. In this embodiment the catheter 102 has a length of 50 cm and a diameter of 3 mm and connects with the balloon 101 at a port 210 of the balloon 101.

The use of two consecutive, sequential tapering sections 101a, 101b avoids sharp changes in the balloon diameter and seeks to eliminate or reduce the possibility of blood damage. It additionally provides a gradual reduction/expansion in the balloon's diameter which achieves higher volume than would be available with a straight reduction/expansion.

In preferred embodiments such as the illustrated embodiment, the balloon 101 includes a substantially non-tapered section 101c that is preferably cylindrical about the longitudinal axis of the balloon 101. In preferred embodiments, the length of the substantially non-tapered section 101c is $>= \frac{1}{3}$ of the longitudinal length of the balloon.

One benefit of having a substantially non-tapering section is that balloon volume is maximised—while the tapering sections have their advantages, the more of the longitudinal length of the balloon that is tapered, the greater the reduction in volume of the balloon when inflated. The larger the balloon volume, the greater the volume of blood displaced during inflation and potentially the greater pressure generated during diastole, enhancing the potential of increasing coronary flow. Additionally, larger balloon volume will have a greater reduction in aortic pressure during deflation.

Having a substantially non-tapering (preferably cylindrical) section at one end of the balloon in combination with the tapered section at the other end has two effects:
1) It acts as a trapper to the volume of blood displaced due to the cross-sectional area differential between the two ends of the balloon. This would lead to an increase in aortic pressure during inflation.
2) The design intent is to manipulate the flow distribution on either side of balloon ends; something that could not be done with a straight cylindrical balloon.

It will be appreciated that the dimensions of the balloon may be varied and different sized balloons may be produced to allow selection by the clinician depending on the subject being treated.

It will be appreciated that the relative positioning of non-tapering and tapering sections along the length of the balloon may be varied. For example, there may be two different tapers (one or both of which may be formed of sections of differing tapering angles). The tapers may be interposed by a non-tapering section. Alternatively, the non-tapering section may be at the first or second end of the balloon.

Although the substantially tapered section 101a is illustrated as ending at a point, it will be appreciated that this is not essential and the second end may be blunted.

With reference to both FIG. 1 and FIG. 2a, the IAB 100 is positioned so that the first end 201 of the balloon 101 is further downstream, and thus at a lower height, than the second end 202 (which is closer to the heart 130). It is to be noted that patients in intensive care are often not lying horizontally but are instead nursed in a semi-recumbent position, with the torso angled at say 30°, so that the head of the patient 120 is elevated to a higher level than the feet of the patient 120 (the semi-recumbent position is often used to reduce the risk of pneumonia).

Figure 2B:
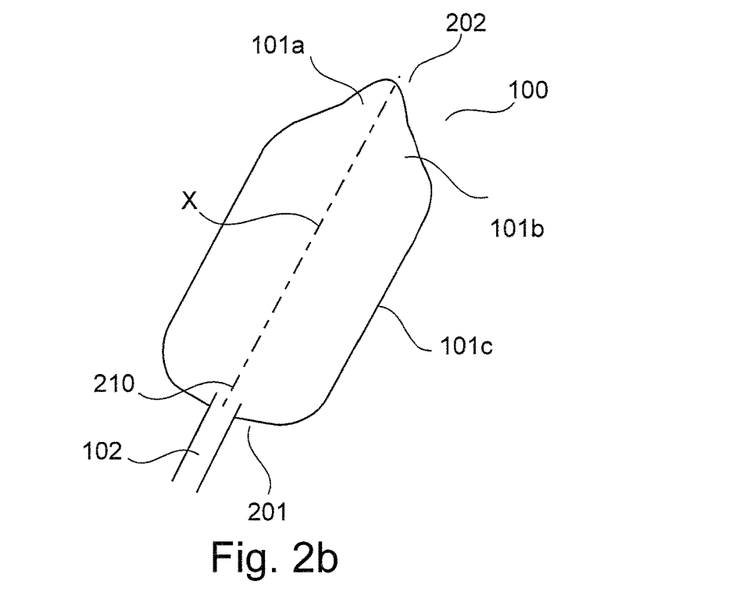
FIG. 2b is a cross-sectional view of an IAB according to an alternate embodiment.

FIG. 2b is a cross-sectional view of an IAB according to an alternate embodiment of the present invention.

In this embodiment, the balloon 101 has a first end 201 and a second end 202 and a port 210 at the first end engaging a catheter 102 for receiving an inflation fluid into the balloon 101'.

The balloon 101 has one or more exterior walls defining, along the length x of the balloon 101 when the balloon is inflated, a first taper 101a narrowing towards the first end 201 and a second taper 101b. The length of the second taper 101b is greater than the length of the first taper 101a.

There may be a rounding at the base of the non-tapered section 101c where it gathers to meet the catheter 102 at the port 210.

Figure 3A:
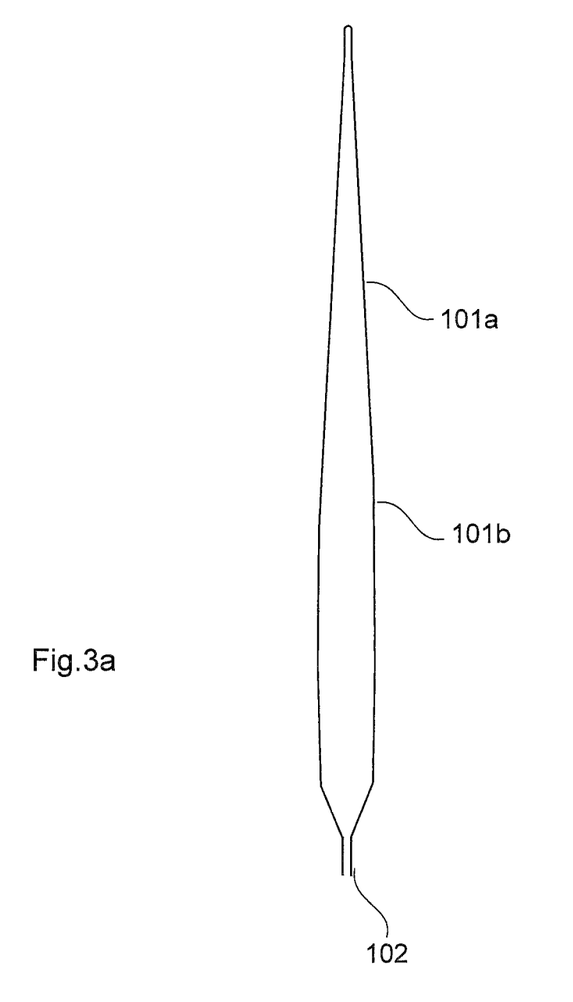
FIGS. 3a, 3b and 3c are sectional views of IABs according to alternate embodiments.
Figure 3B:
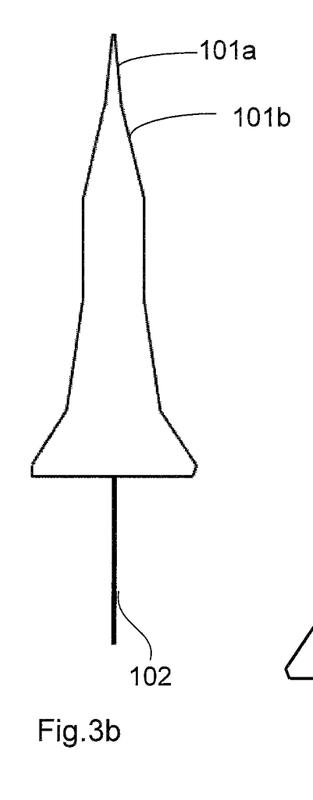
Figure 3C:
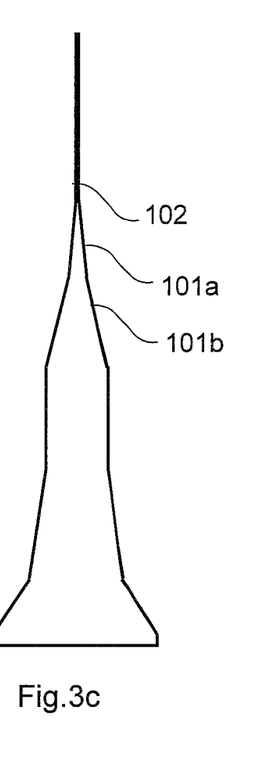

FIGS. 3a, 3b and 3c are sectional views of IABs according to alternate embodiments.

In each case, the balloon is illustrated when it is substantially fully inflated at the standard operating pressure.

As shown in FIGS. 3a-3c, the balloon may have a first taper and tapers via two or more tapering sections along the length of the balloon towards one of the first or second ends. In a preferred embodiment, the balloon includes a second taper having one or more tapering sections that taper along the length of the balloon towards the other of the first or second ends.

For example, FIG. 3a shows the first and second tapers contracting towards their respective ends.

FIG. 3b shows the first taper contracting towards its respective end and the second taper expands towards its respective end. FIG. 3c shows an alternative arrangement of the embodiment of FIG. 3b in which the port for the catheter is positioned at the opposing end to that of FIG. 3b. It will be appreciated that this principle can be applied to all of the balloons described—the port for the catheter can be positioned at either end.

Having the catheter positioned at the end of the balloon proximal to the heart may provide advantages in certain situations. For example, since inflation begins mostly from the tip, the largest part of the balloon could displace higher volumes towards the heart. Similarly, although this largest part of the balloon will deflate later, it can generate a large suction wave that is closer to the heart, and hence may generated a beneficial reduction in after load.

In another embodiment, a catheter port may be provided at both longitudinal ends of the balloon and a plug may be used to seal the end that does not receive the catheter. In this way, the balloon could be used in either orientation with the taper being proximal or distal to the heart. The plug may, for example, be a hard foam or plastics material and may be covered/plated with of a biocompatible material. There may be a lip on the bung as well as the port, optionally with an incorporated o-ring to aid in sealing. The bung may be covered with the same material as that of the balloon.

Figure 4A:
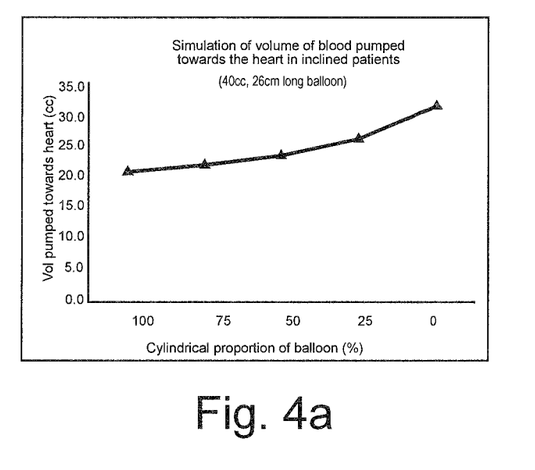
FIG. 4a is a graph illustrating calculations for pumping volume achieved by embodiments of the present invention having different tapered proportions.

FIG. 4a is a graph showing calculated/simulated values of pumping volumes to illustrate the improvement in effectiveness of embodiments of the present invention as the proportion of the overall IAB length occupied by the tapered region is increased. This data has been generated as follows;

a set of in-vitro experiments were conducted in which certain specific IAB geometries were tested in an inclined artificial aorta simulating a patient at the semi-recumbent position.

values for intermediate geometries have then been calculated/simulated, in order to interpolate between the specific test cases.

In all cases illustrated in the graph, the balloon volume and length are 40 cc and 26 cm respectively and the balloon is formed from silicone having a modulus of elasticity of approximately 1.4 MPa.

As the tapered region increases in length, the maximum diameter of the balloon must increase in order to maintain the same total volume, and thus at after a certain point (approximately where the tapered section is 75% of the length of the balloon), the required diameter of the balloon will exceed the acceptable physiological range of sizes of IABs that can be accommodated in a typical aorta.

In one embodiment, the length of the tapered section 101a is 50% of the total length, at which point the inflated diameter at the non-tapered section is approximately 1.7 cm. This is within an acceptable physiological range for a 40 cc IAB, and as can be seen, the volume of blood flow towards the heart is increased in the region of 15%. This equates to an approximately 50% reduction in the loss of pumping efficiency that would be experienced by a conventional balloon in the same circumstances.

In the above described embodiments, the IAB also provides reduced resistance to blood flow being drawn away from the heart due to balloon deflation. The Poiseulle equation states that flow resistance is inversely related to the quadratic power of the hydraulic diameter, as follows:

$$R = \frac{8\mu\delta x}{\pi r^4}$$

Where R is the resistance, $\mu$ is viscosity, $\delta x$ is the length of the considered portion and r is the hydraulic radius. Therefore, a comparison between the resistance presented by an equal length of the above portion of traditional cylindrical balloon and that of the embodiments of FIGS. 2a and 2b, yields a ratio that is inversely related to their corresponding mean diameter along $\delta x$ of each balloon.

$$\frac{R_1}{R_2} = \frac{(r_{aorta} - r_2)^4}{(r_{aorta} - r_1)^4},$$

Where $R_1$ and $R_2$ are the resistance of the traditional and new shaped balloons respectively, $r_{aorta}$ is the radius of the aorta at the portion considered, $r_1$ and $r_2$ are the radii of the traditional and new shaped balloons respectively.

Realistic assumptions of $r_{aorta}=1.1$ cm, $r_1=0.8$ cm, and average radius along the tapered section $r_2=0.42$ cm indicates the resistance of the traditional balloon is much higher than that of the embodiments of FIGS. 2a and 2b.

In selected optional embodiments of the present invention described below, the balloon 101 is arranged to preferentially inflate from the first end 201 towards the second end 202, i.e. from bottom to top.

An advantage of the IAB 100 preferentially inflating generally from bottom to top (i.e. from a portion of the aorta 110 that is relatively distant from the heart 130 to a portion of the aorta 110 that is in relative proximity to the heart 130) is that the inflation of the IAB 100 results in an improved pumping action compared to some prior art (cylindrically shaped) balloons. This pumping action better augments the flow of blood towards the coronary arteries when the balloon 101 is horizontal. The preferential inflation towards the heart is also less affected by hydrostatic pressure when the torso is angled.

Figure 4B:
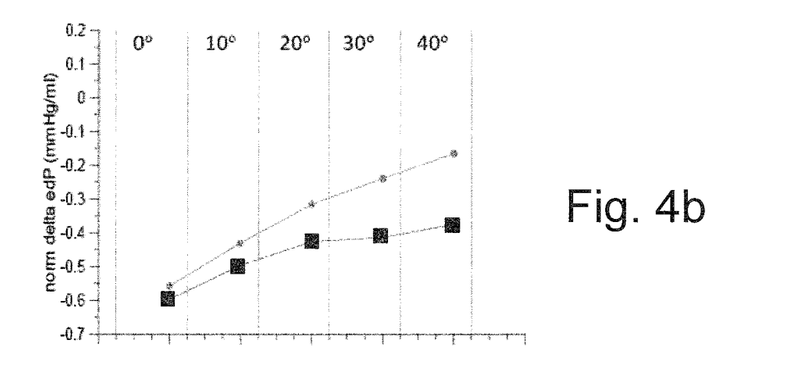
FIGS. 4b and 4c are graphs showing in-vitro results.
Figure 4C:
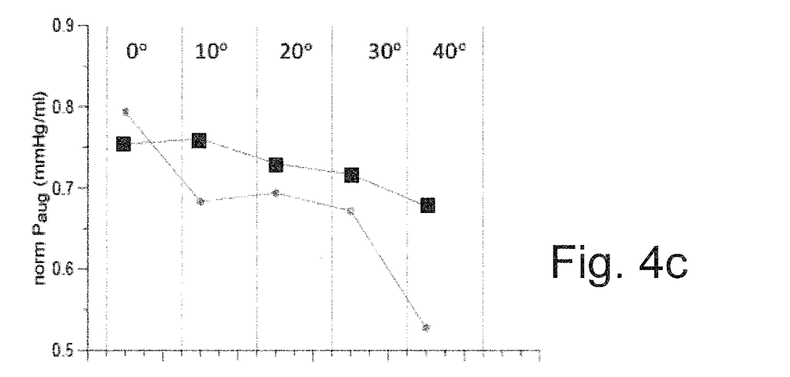

FIGS. 4b and 4c are graphs showing in-vitro results.

In FIG. 4b, square and circular marks indicate a two thirds taper decreasing diameter (⅔ TDD) balloon and a conventional cylindrical balloon respectively. The results show that the tapering balloon provides better reduction of end diastolic pressure due to deflation. The X axis shows normalised delta end-diastolic pressure (how well pressure is reduced). The results also show the tapering balloon is less affected by angulation (Y axis showing angle of inclination of patient).

In FIG. 4c, square and circular marks indicate the two thirds taper increasing diameter (⅔ TID) balloon and a conventional cylindrical balloon, respectively. The results show that the tapering balloon provides better increase of augmenting pressure due to inflation. The Y axis shows normalised augmentation pressure. The results also show the tapering balloon is less affected by angulation (Y axis showing angle of inclination of patient).

In vitro experiments performed by the inventor using traditional and tapered balloons were conducted to simulate the semi-recumbent position at which patient in intensive care units are nursed. It was confirmed that balloons with a taper proximate the aorta were less sensitive to the change of angle of the recumbent patient.

Methods: 4 traditional cylindrically shaped IABs (25, 34, 40 and 50 cc, Datascope) and a tapered IAB with decreasing diameter from the catheter to the tip (36 cc, Datascope) were tested in a mock circulation with a 1:1 size replica silicon aorta. The aorta was placed on a platform allowing angles of 30°, 45°, 65° and 75°, under physiological pressure and compliance, 60 mmHg and 1.63 ml/mmHg. Flow was measured on either side of the balloon with snug-fit flow probes.

Results: At the horizontal position the percentage of each balloon volume displaced towards the coronary arteries was higher in the IAB with decreasing diameter than any other IAB. In all IABs, the flow volume displaced towards the coronary arteries was reduced when the aorta was at an angle; with progressive reduction as the angulations increased for only the cylindrically shaped IABs. The tapered IAB was less sensitive to the change in angle and the reduction in volume displacement towards the coronary arteries with increasing angulation was less than any other IAB.

Conclusion: The in vitro results show that IAB performance is affected by increasing angulation and such effect can be counterbalanced by varying the shape of the balloon.

Figure 5:
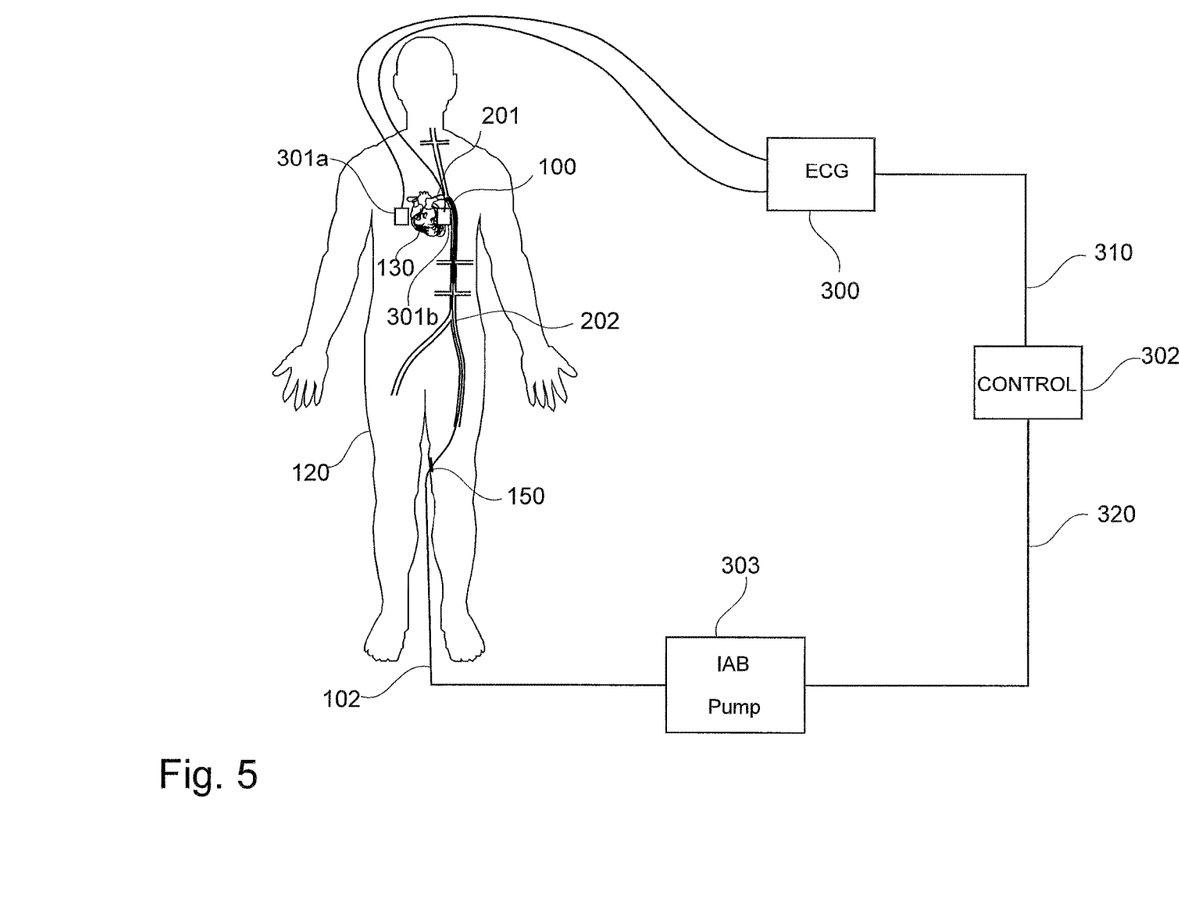
FIG. 5 is a schematic diagram of a system according to an embodiment of the present invention.

FIG. 5 shows a system according to an embodiment, and shows an electrocardiogram (ECG) apparatus 300, ECG electrodes 301a, 301b, a controller 302 and an IAB pump 303.

The ECG apparatus 300 detects the electrical action potentials of the heart 130 using the ECG electrodes 301a, 301b. FIG. 4 shows only two ECG electrodes although as those skilled in the art will appreciate, a different number of electrodes may be used (for example 12 electrodes). The ECG 300 outputs a signal 310 which represents the electrical activity of the heart 130.

The controller 302 receives the signal 310 and outputs a signal 320 which controls the IAB pump 303. The IAB pump 303 pumps an inflation fluid to inflate the IAB 100. In this embodiment, the IAB pump 303 pumps helium gas. Helium gas is preferred due to its low viscosity which allows the helium to readily flow along the catheter 102 although in alternative embodiments other liquids or gases could be used instead of helium gas.

In this embodiment, the controller 302 is arranged to control the IAB pump 303 so that the IAB 100 counter-pulsates every heartbeat (1:1). On every heartbeat, the IAB 100 is inflated (i.e. the IAB pump 303 pumps helium gas along the catheter 102 into the balloon 101 to inflate the IAB 100) during diastole so that the coronary flow is augmented. During systole, the IAB pump 303 allows the helium gas to return from the balloon 101 (the pressure of the helium gas inside the balloon may be of the order of hundreds of millimeters of mercury) along the catheter 102 back into the IAB pump 303.

As those skilled in the art will appreciate, in other embodiments the IAB 100 may be inflated, for example, every second heartbeat (1:2), every third heartbeat (1:3) or in some other ratio, e.g. 2:3. In yet other embodiments, the IAB 100 may be inflated slightly before diastole, or even during systole.

Figure 6:
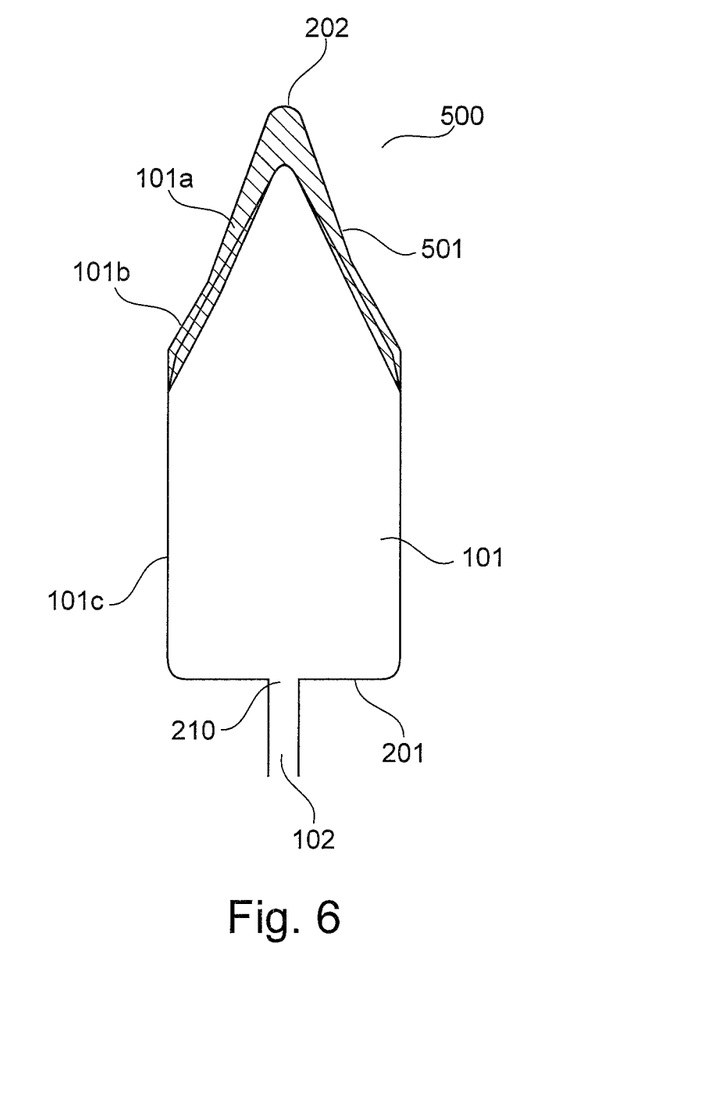
FIG. 6 is a cross-sectional view of another embodiment of the present invention, and shows that the walls of an IAB are non-uniform so that the IAB preferentially inflates from one end to the other end.

FIG. 6 is a cross-sectional view of an embodiment, in which the walls of the IAB 500 are non-uniform so that the IAB preferentially inflates from the first end 201 towards the second end 202. The IAB 500 comprises a balloon 501 and a catheter 102; the catheter 102 connects to the balloon at the first end 201 of the IAB 500.

Most IABs in common use are manufactured from polymers of relatively high elastic modulus such that, during normal operation, they do not exhibit any significant elasticity. In this embodiment, elasticity is an important property and is referred to, in the foregoing, as a material having low elastic modulus.

When not inflated, the balloon 501 is generally furled. The balloon 501 in this embodiment is made of an elastic polymer and has walls that are relatively thin at the first end 201 and relatively thick at the second end 202. When inflated with an inflation fluid, the balloon 501 expands preferentially at the first end 201 due to the relatively thin walls at the first end 201. Continued inflation of the balloon 501 causes the second end 202 to become stretched, with the result that the balloon 501 eventually adopts a generally tapered shape. In so doing, the effectiveness of the balloon is increased by the action of an advancing front travelling along the IAB in the opposite direction to normal blood flow. When the inflation fluid is allowed to return from the balloon 501 to the IAB pump 303 the IAB 500 returns to its collapsed shape.

In an alternative embodiment, the IAB 500 has walls that are of substantially constant thickness but the balloon is made from two pieces of elastic polymer with different characteristics. The first end 201, up until about halfway along the balloon, is made of an elastic polymer that stretches relatively easily but once the elastic polymer has stretched by, say, 100%, it becomes significantly more difficult to stretch the elastic polymer further. The second end 202, down until about halfway along the balloon, is made of an elastic polymer that takes more effort to stretch (than the elastic polymer of the first end 201) but the elastic polymer of the second end 202 maintains its ability to be stretched until it has been stretched by 250%, at which it also becomes significantly more difficult to stretch.

Figure 7:
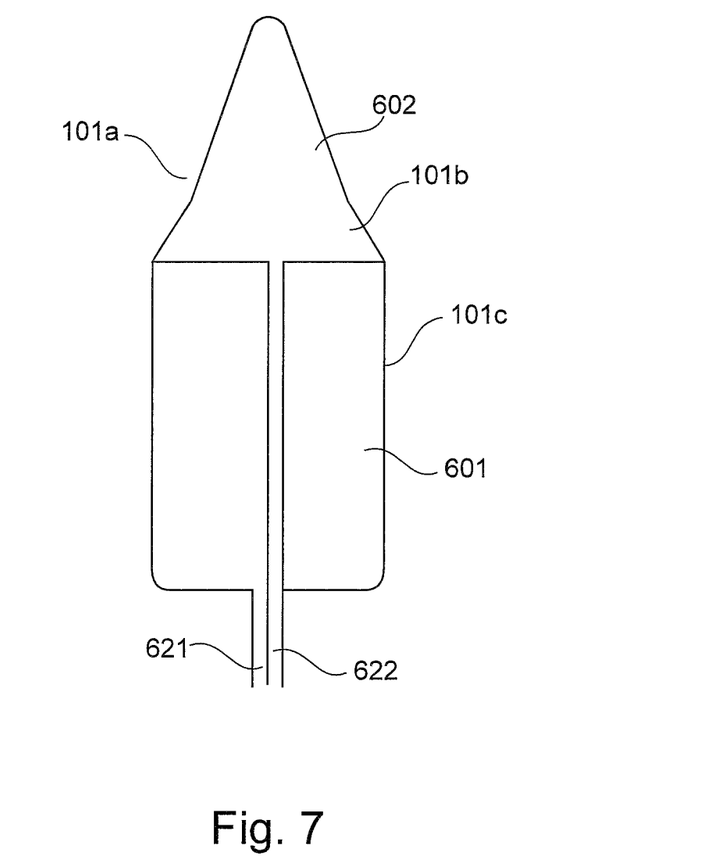
FIG. 7 is a cross-sectional view of another embodiment of the present invention, and shows an IAB with two chambers, each with a respective catheter.

FIG. 7 is a cross-sectional view of another embodiment, in which an IAB 600 has two chambers 601, 602, each with a respective catheter 621, 622.

The chambers 601, 602 can (due to the separate catheters 621, 622) be inflated to different extents and thus when inflated the IAB 600 adopts a shape similar to the IAB of FIG. 4 which approximates a taper. In this embodiment the balloon 601 has a length of 6 cm and a radius (before inflation) of 0.7 cm while the balloon 602 has a length of 20 cm and a radius (before inflation) of 0.7 cm.

Whereas the system of FIG. 5 showed a single IAB pump 303, the IAB 600 requires two IAB pumps 303, one for each balloon 601, 602. The use of two IAB pumps 303 allows improved control of the inflation characteristics of the IAB 100 compared to the IAB 100 as the timing of the inflation of the balloons 601, 602 is controlled by the IAB pumps and not by the physical characteristics of the IAB 600 (in contrast, the inflation of the IAB 100 was controlled by the shape of the IAB 100 and the shape of the IAB 500 was controlled by the material properties at the ends of the IAB 500). Thus to augment the coronary flow, the balloon 602 is inflated slightly after the inflation of the balloon 601. Additionally, the balloon 601 is inflated more than the balloon 602 so that the balloon 602 expands to a diameter of 1 cm whereas the balloon 601 expands to a diameter of 1.5 cm.

In alternative embodiments, the IAB 600 may have 3 or more chambers or balloons, each with a respective flexible catheter. In yet other embodiments, the IAB 600 may have a tapered shape before inflation.

In other alternative embodiments, the IAB pump may be modified by incorporating one or more valves (e.g. solenoid controlled valves) so that a single modified IABP can be used to control the inflation/deflation of two or more chambers 601, 602.

Figure 8:
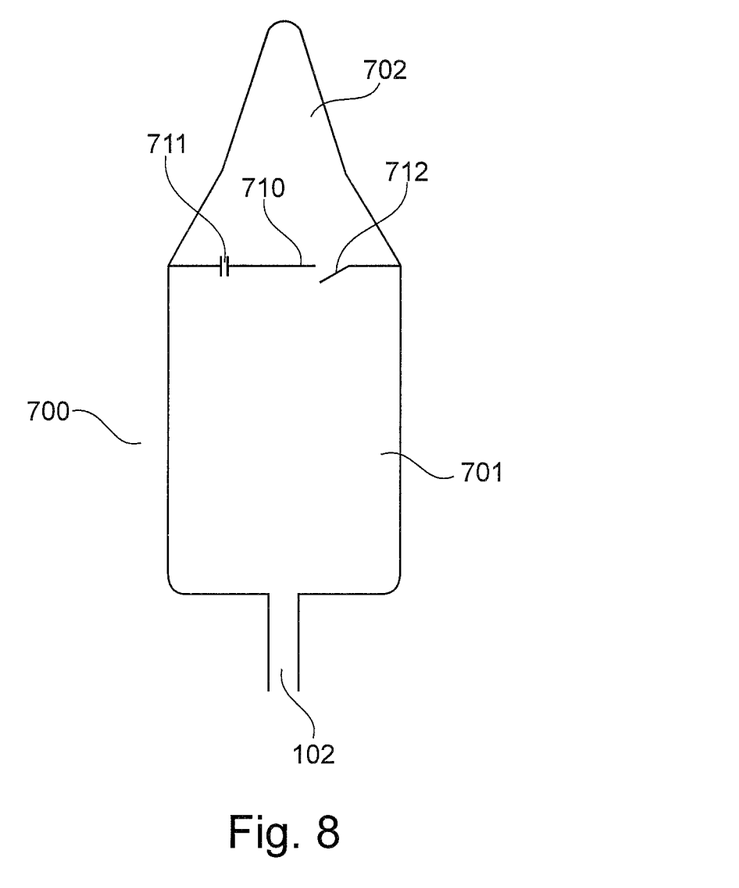
FIG. 8 is a cross-sectional view of another embodiment of the present invention, and shows an IAB with a balloon divided into two chambers which communicate via an orifice and a valve.

FIG. 8 is a cross-sectional view of another embodiment, in which an IAB 700 has a balloon divided into two chambers 701, 702 by a septum 710. The septum 710 has an orifice 711 and a one-way valve 712 which allow an inflation fluid to communicate between the two chambers 701, 702. The one-way valve 712 allows an inflation fluid to readily flow from the chamber 702 to the chamber 701 but substantially prohibits an inflation fluid from flowing from the chamber 701 to the chamber 702. In this embodiment the IAB 700 has a generally tapered shape before inflation.

During inflation by an inflation fluid, the chamber 701 receives the inflation fluid directly from the catheter 102. The chamber 702 receives the inflation fluid indirectly, from the chamber 701 via the orifice 711 (the one-way valve 712 does not allow any significant quantity of inflation fluid to flow from the chamber 701 to the chamber 702). The orifice 711 has the effect that the chamber 701 is inflated by the inflation fluid before the chamber 702 is inflated.

During deflation, inflation fluid in the chamber 701 is expelled directly along the catheter 102. Inflation fluid in the chamber 702 can pass through the orifice into the chamber 701 and can additionally pass through the one-way valve 712 into the chamber 701. Thus in contrast to the situation during inflation, the chamber 702 can be deflated substantially simultaneously with the chamber 701 and at substantially the same rate as the chamber 701.

In alternative embodiments, the orifice 711 may be replaced with a combined orifice and one-way valve that allows an inflation fluid to flow only from the chamber 701 to the chamber 702 but limits the rate at which the inflation fluid may flow from the chamber 701 to the chamber 702. The one-way valve 712 may also be combined with a respective orifice. Thus in some embodiments the inflation and deflation characteristics of the chamber 702 are controlled by respective orifices that are combined with respective one-way valves.

In yet other embodiments, the one-way valve 712 may be omitted. However, use of the one-way valve 712 is preferred to allow more rapid deflation of the chamber 702.

In yet further embodiments, two separate balloons may be used instead of a common balloon divided by a septum 710 into two chambers 701, 702.

In other embodiments, the chambers 701, 702 (or separate balloons, in embodiments in which separate balloons are used instead of chambers) may be formed from two or more pieces of elastic polymer, where the two or more pieces have different characteristics. As discussed above in connection with an alternative embodiment of FIG. 6, the first end 201 (up until about halfway along the balloon) may be formed from an elastic polymer having a first set of mechanical properties whereas the second end 202 (down until about halfway along the balloon) may be formed from an elastic polymer having a second set of mechanical properties.

In an alternative embodiment, the IAB 500 has walls that are of substantially constant thickness but the balloon is made from two pieces of elastic polymer with different characteristics. The first end 201 is made of an elastic polymer that stretches relatively easily but once the elastic polymer has stretched by, say, 100%, it becomes significantly more difficult to stretch the elastic polymer further. The second end 202 is made of an elastic polymer that takes more effort to stretch (than the elastic polymer of the first end 201) but the elastic polymer of the second end 202 maintains its ability to be stretched until it has been stretched by 250%, at which it also becomes significantly more difficult to stretch.

In one embodiment, one or more of the tapering sections may be formed from one or more balloons that step up or down in order to form the tapering section having the substantially constant angle of tapering.

It will be appreciated that features of the various embodiments described are complementary and can be combined or inter-changed as needed. For example, differing thickness walls could be used with balloons of different shapes or configurations.

The invention claimed is:

1. A medical balloon for a balloon pump, the medical balloon comprising a single balloon having a first end and a second end and a port at one of the ends for engaging a catheter for receiving an inflation fluid into the balloon, the balloon having an exterior wall defining, when the balloon is inflated at substantially a standard operating pressure, a taper along at least a part of a length of the balloon, the taper having a first tapering section directly adjoined to a second tapering section, each of the first tapering section and the second tapering section having a different, substantially constant, angle of tapering, the balloon being substantially asymmetrical about a mid-point between the first and second ends when inflated.

2. A medical balloon as claimed in claim 1, wherein the balloon is fully inflated at the standard operating pressure.

3. A medical balloon as claimed in claim 1, wherein the taper is a first taper and tapers along the length of the balloon towards one of the first or second ends, the balloon further comprising a second taper having one or more tapering sections that taper along the length of the balloon towards the other of the first or second ends.

4. A medical balloon as claimed in claim 3, wherein the first taper expands towards its respective end and the second taper contracts towards its respective end.

5. A medical balloon as claimed in claim 3, wherein the first taper contracts towards its respective end and the second taper expands towards its respective end.

6. A medical balloon as claimed in claim 3, wherein the first and second tapers contract towards their respective ends.

7. A medical balloon as claimed in claim 3, wherein the first and second tapers expand towards their respective ends.

8. A medical balloon as claimed in claim 1, the exterior wall further defining, when the balloon is inflated at substantially a standard operating pressure, a substantially non-tapering section, the substantially non-tapering section being at least ⅓ the length of the balloon.

9. A medical balloon as claims in claim 1, wherein the exterior wall thickness increases along at least a part of the length of the balloon.

10. A medical balloon as claimed in claim 9, wherein the exterior wall thickness increases towards the second end.

11. A medical balloon as claimed in claim 1, wherein the balloon is adapted for preferential inflation from the first end to the second end.

12. A medical balloon as claimed in claim 1, wherein the balloon comprises an elastic polymer.

13. A medical balloon as claimed in claim 1, wherein the balloon comprises two or more portions, and wherein the two or more portions are formed from elastic polymers having different mechanical properties.

14. A medical balloon as claimed in claim 1, wherein the balloon comprises a single chamber.

15. A medical balloon as claimed in claim 14, wherein the one or more septa include one or more one-way valves.

16. A medical balloon as claimed in claim 1, wherein the balloon comprises two or more chambers separated by one or more septa.

17. A medical balloon as claimed in claim 16, wherein the one or more septa include one or more orifices.

18. An intra-aortic medical pumping balloon comprising a single balloon having a first end and a second end and a port at one of the ends to engage a catheter, wherein upon receiving an inflation fluid via the catheter to inflate the balloon to a standard operating pressure, an exterior wall of the balloon defining a taper along at least a part of a length of the balloon, the taper having a first tapering section directly adjoined to a second tapering section, each of the first tapering section and the second tapering section having a different, substantially constant, angle of tapering, the balloon being substantially asymmetrical about a mid-point between the first and second ends when inflated.

* * * * *